(12) United States Patent
Vajda et al.

(10) Patent No.: US 8,148,293 B2
(45) Date of Patent: Apr. 3, 2012

(54) SUBNANOMETER AND NANOMETER CATALYSTS, METHOD FOR PREPARING SIZE-SELECTED CATALYSTS

(75) Inventors: Stefan Vajda, Lisle, IL (US); Michael J. Pellin, Naperville, IL (US); Jeffrey W. Elam, Elmhurst, IL (US); Christopher L. Marshall, Naperville, IL (US); Randall A. Winans, Downers Grove, IL (US); Karl-Heinz Meiwes-Broer, Roggentin (GR)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 12/869,459

(22) Filed: Aug. 26, 2010

(65) Prior Publication Data
US 2011/0045969 A1 Feb. 24, 2011

Related U.S. Application Data

(63) Continuation of application No. 12/402,948, filed on Mar. 12, 2009, which is a continuation-in-part of application No. 12/610,897, filed on Nov. 2, 2009, which is a continuation-in-part of application No. 10/941,800, filed on Sep. 14, 2004, now Pat. No. 7,625,840.

(60) Provisional application No. 60/503,668, filed on Sep. 17, 2003, provisional application No. 61/069,041, filed on Mar. 12, 2008.

(51) Int. Cl.
| | |
|---|---|
| *B01J 23/00* | (2006.01) |
| *B01J 21/00* | (2006.01) |
| *B01J 20/00* | (2006.01) |
| *B01J 29/00* | (2006.01) |
| *B01J 37/00* | (2006.01) |

(52) U.S. Cl. ........ 502/334; 502/300; 502/327; 502/339; 502/342; 502/350; 502/351; 502/352; 502/355; 502/415; 502/439; 977/810

(58) Field of Classification Search .................. 502/300, 502/327, 334, 339, 342, 343, 350, 351, 352, 502/355, 415, 439; 977/810
See application file for complete search history.

(56) References Cited

U.S. PATENT DOCUMENTS 3,953,368 A * 4/1976 Sinfelt .......................... 502/223
(Continued)

OTHER PUBLICATIONS

Argyle, M.D., et al., Effect of Catalyst Structure on Oxidative Dehyrogenationof Ethane and Propane on Alumina-Supported Vanadia. J. Catal, 208, p. 139-140 (2002).

(Continued)

*Primary Examiner* — Cam N. Nguyen
(74) *Attorney, Agent, or Firm* — Cherskov Flaynik & Gurda, LLC

(57) ABSTRACT

Highly uniform cluster based nanocatalysts supported on technologically relevant supports were synthesized for reactions of top industrial relevance. The Pt-cluster based catalysts outperformed the very best reported ODHP catalyst in both activity (by up to two orders of magnitude higher turnover frequencies) and in selectivity. The results clearly demonstrate that highly dispersed ultra-small Pt clusters precisely localized on high-surface area supports can lead to affordable new catalysts for highly efficient and economic propene production, including considerably simplified separation of the final product. The combined GISAXS-mass spectrometry provides an excellent tool to monitor the evolution of size and shape of nanocatalyst at action under realistic conditions. Also provided are sub-nanometer gold and sub-nanometer to few nm size-selected silver catalysts which possess size dependent tunable catalytic properties in the epoxidation of alkenes. Invented size-selected cluster deposition provides a unique tool to tune material properties by atom-by-atom fashion, which can be stabilized by protective overcoats.

20 Claims, 13 Drawing Sheets

U.S. PATENT DOCUMENTS

| | | | |
|---|---|---|---|
| 4,163,811 A * | 8/1979 | Kohlmayr et al. | 427/115 |
| 4,552,855 A * | 11/1985 | Ozin et al. | 502/74 |
| 4,569,924 A * | 2/1986 | Ozin et al. | 502/184 |
| 5,623,090 A | 4/1997 | Haruta et al. | |
| 6,252,095 B1 | 6/2001 | Hayashi et al. | |
| 6,781,018 B2 | 8/2004 | Liu et al. | |
| 7,138,354 B2 * | 11/2006 | Hampden-Smith et al. | 502/101 |
| 7,235,159 B2 * | 6/2007 | Gu et al. | 204/192.1 |
| 7,354,881 B2 * | 4/2008 | Resasco et al. | 502/185 |
| 7,402,719 B2 | 7/2008 | Brophy et al. | |
| 7,504,355 B2 * | 3/2009 | Carter et al. | 502/300 |
| 7,582,586 B2 * | 9/2009 | Fanson et al. | 502/185 |
| 7,592,290 B2 * | 9/2009 | Hussain et al. | 502/335 |
| 7,713,907 B2 * | 5/2010 | Elam et al. | 502/263 |
| 7,767,610 B1 * | 8/2010 | Coker | 502/60 |
| 2002/0169077 A1 * | 11/2002 | Bae et al. | 502/527.19 |
| 2003/0181321 A1 * | 9/2003 | Hampden-Smith et al. | 502/180 |
| 2003/0186109 A1 * | 10/2003 | Huang et al. | 429/44 |
| 2005/0065026 A1 * | 3/2005 | Okubo | 502/339 |
| 2005/0106435 A1 * | 5/2005 | Jang et al. | 429/30 |
| 2007/0184974 A1 * | 8/2007 | Bates | 502/240 |
| 2008/0039315 A1 | 2/2008 | Ma et al. | |
| 2009/0124488 A1 * | 5/2009 | Hofinger et al. | 502/150 |
| 2009/0264277 A1 * | 10/2009 | Raj et al. | 502/4 |

OTHER PUBLICATIONS

Silberova, B., et al., Oxidative dehyrogenation of ethane and propane at short contact time., Appl. Catal. A: General 276, p. 17-28 (2004).
Viirola, H., "Controlled Growth of Tin Dioxide Thin Films by Atomic Layer Epitaxy", 249 (1994), p. 144-149.
S. Vadja, et al., "Subnanometre Platinum Clusters as Highly Active and Selective Catalysts for the Oxidative Dehydrogenation of Propane", Nature Materials DOL:10.1038/NMAT2384, Feb. 8, 2009.

* cited by examiner

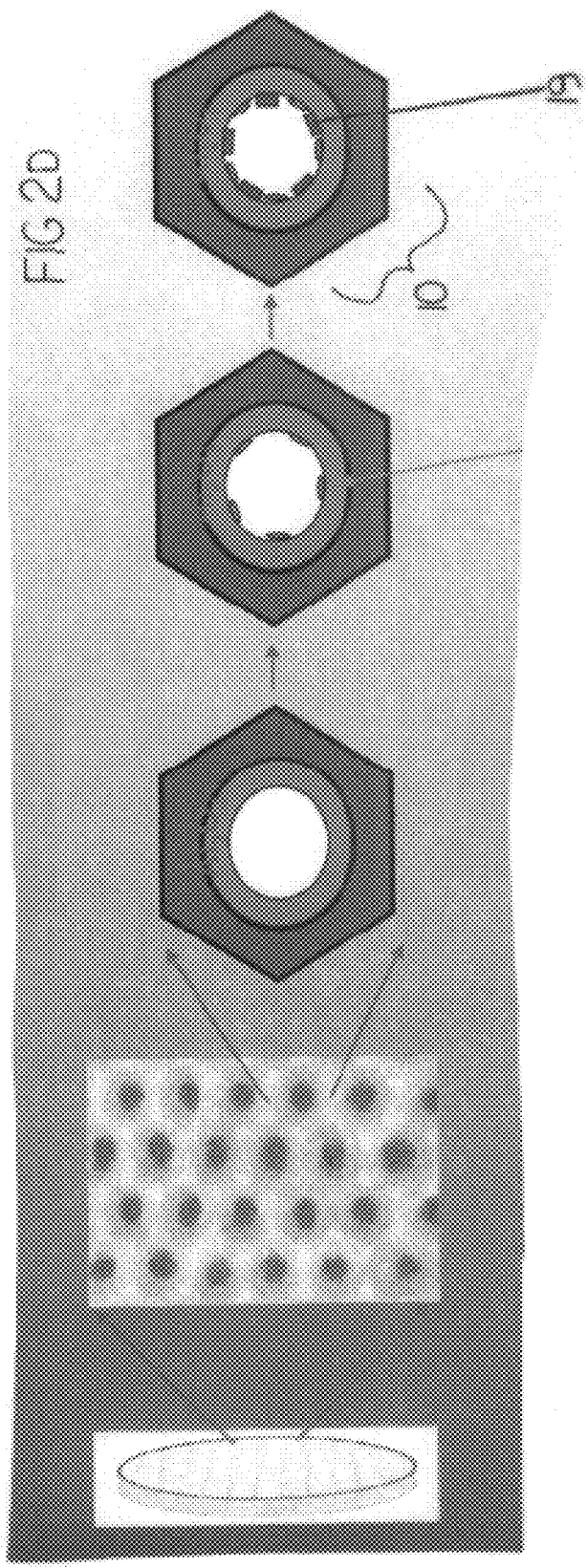

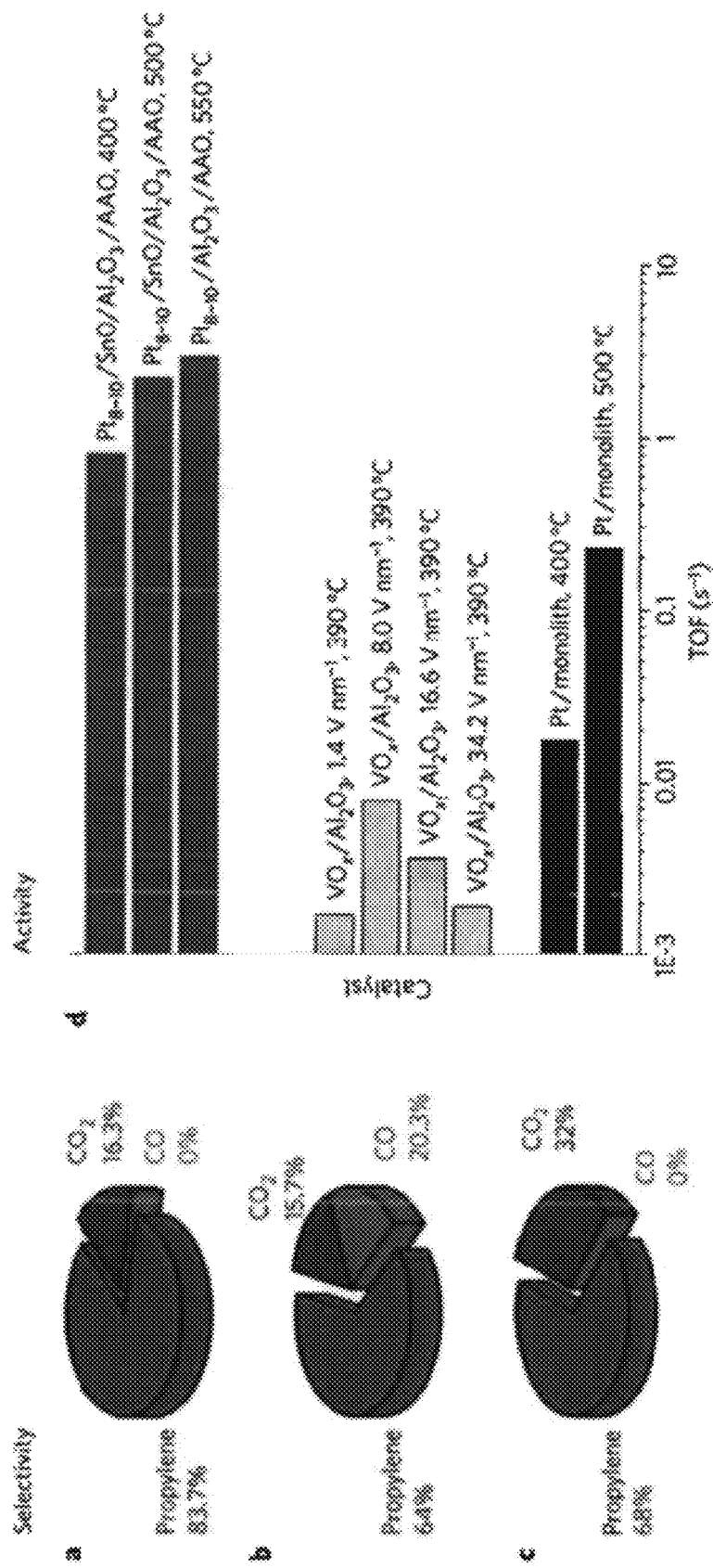
FIGURES 3A-D

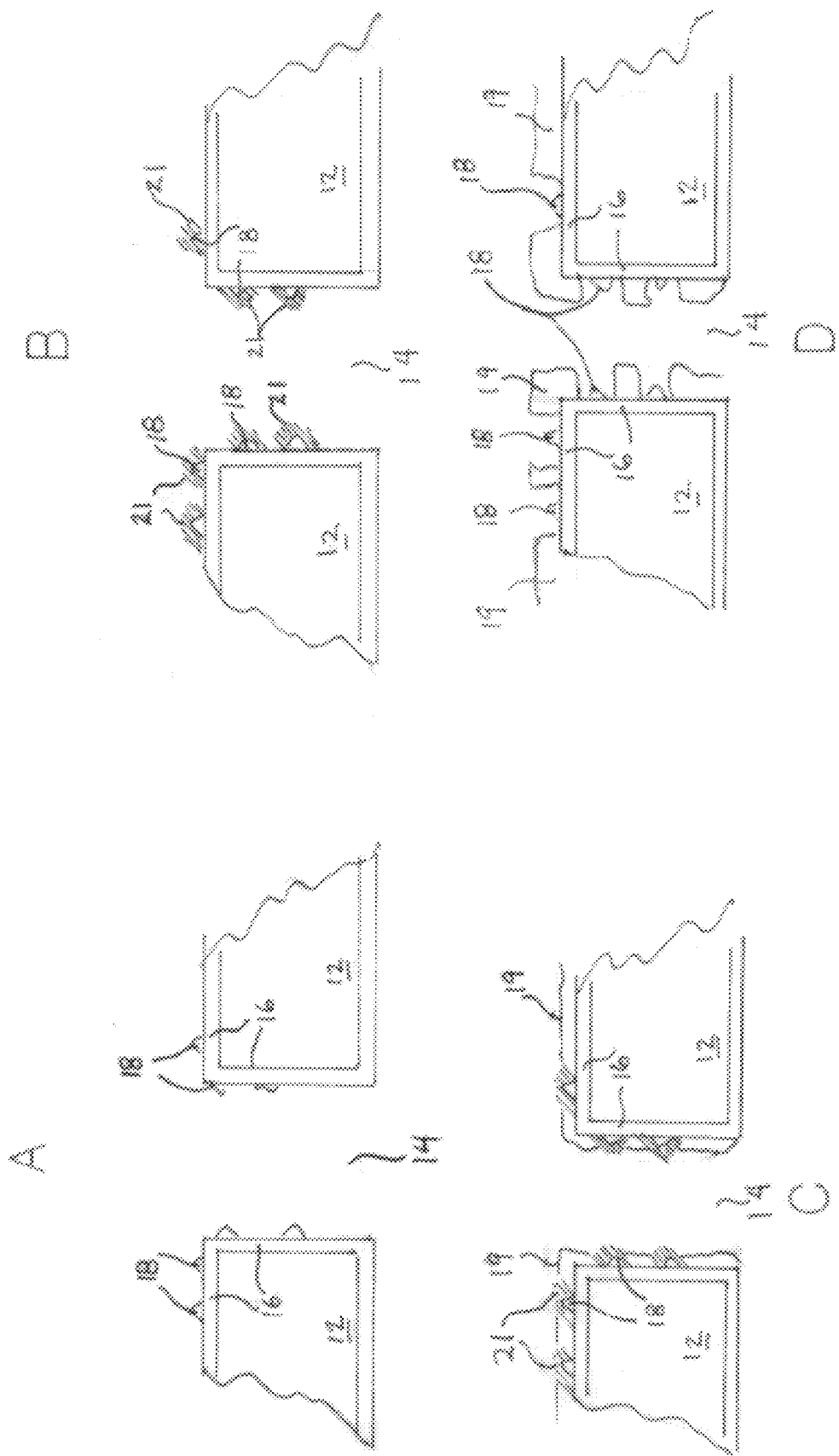

SUBNANOMETER AND NANOMETER CATALYSTS, METHOD FOR PREPARING SIZE-SELECTED CATALYSTS

This Utility Patent Application claims priority as a continuation of, and hereby incorporates by reference, U.S. application Ser. No. 12/402,948 filed on Mar. 12, 2009, currently pending, which claims the benefit of U.S. Provisional Patent Application No. 61/069,041 filed on Mar. 12, 2008. This Application further claims the benefit of priority as a continuation in part of U.S. application Ser. No. 12/610,897 filed on Nov. 2, 2009, currently pending, which is a continuation in part of U.S. Utility patent application Ser. No. 10/941,800 filed on Sep. 14, 2004, currently registered as U.S. Pat. No. 7,625,840, which in turn claimed the priority benefit of U.S. Provisional Application Patent Application No. 60/503,668 filed on Sep. 17, 2003.

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

1. Field of the Invention

This invention relates to subnanometer catalysts and methods for fabricating subnanometer and nanometer size-selected catalyst clusters, and more specifically, this invention relates to catalyst clusters comprising 4 to 20 atoms of catalytic metal and methods of producing the clusters on a support substrate.

2. Background of the Invention

Alkanes are typical feedstocks for transformation to alkenes, aromatics and chemicals containing value added moieties. Dehydrogenation is a route to such transformations but dehydrogenation is an endothermic process requiring significant energy input.

Oxidative dehydrogenation (ODH) of propane to propylene is a multibillion dollar industrial process. Two classes of catalysts are used: VOx and Pt-based. The vanadia based ones are highly selective but their activity is relatively low. Pt-based catalysts are more active but their selectivity is low. U.S. Pat. No. 6,781,018 issued to Liu et al. on Aug. 24, 2004 discloses the use of molybdenum and/or vanadium oxides for converting dimethyl ether to formaldehyde.

ODH of alkanes is exothermic, and thus an attractive alternative to dehydrogenation. However, current ODH catalysts have limited activity and/or poor selectivity resulting from inability to prevent complete oxidation. For example, FIG. 1 depicts a preferable reaction pathway "A" for propane undergoing oxidative dehydrogenation versus just as likely non-preferable reaction pathways "B", "C", "D", and "E".

Silberova et al. *Appl. Catal. A: General* 276 17-28 (2004) discusses oxidative dehydrogenation of ethane and propane at short contact times.

U.S. Pat. No. 5,623,090 issued to Haruta et al on Apr. 22, 1997 discloses catalysts comprising gold particles deposited on titanium oxide carrier. These catalysts were used to produce alcohol, ketone, and epoxides via oxidation of hydrocarbons.

U.S. Pat. No. 6,252,095 issued to Hayashi et al on Jun. 26, 2001 also utilizes gold particles to partially oxidize unsaturated hydrocarbons.

The configuration of catalyst support surfaces also has been investigated. U.S. Pat. No. 7,402,719 issued to Brophy et al on Jul. 22, 2008, discloses the use of 1-2 millimeter diameter channels containing catalysts to facilitate catalytic dehydrogenation. However, the short contact times embodied by Brophy results in relatively low product selectivities, for example 18 percent in the case of propylene formation.

U.S. Patent Publication Number 2008/0039315 by Ma et al, published on Feb. 14, 2008, discloses the use of nanotubes containing catalysts. A drawback to this configuration is a lack of control as to size of catalyst clusters and reaction sites, inasmuch as wet chemistry is utilized to combine the support substrate with catalyst material. This results in different size distributions, and poorer selectivity. Also, the less than 5 nm pore sizes of Ma can result in clogging of reaction-ways.

A need exists in the art for catalysts and a method for supporting catalysts which exhibit high reactivity and selectivities of greater than 50 percent. The catalysts should not require a constant input of energy to operate. Also, the catalysts should operate on selective moieties in a chemical system so as to optimize conversion rates without the generation of unwanted products. Finally, the catalysts should exhibit superior reactivity and selectivities at lower temperatures than typical catalyst operating temperatures.

SUMMARY OF THE INVENTION

An object of the present invention is to provide a catalyst and a method for supporting catalysts that overcomes many of the disadvantages of the prior art.

Another object of the present invention is to provide a catalyst which exhibits high activity levels and selectivities. A feature of the invented catalyst is that each cluster of metal comprising a reactive center consists of 8 to 10 metal atoms. An advantage of the invented catalyst is that each of the atoms directly contact reactants to be transformed.

Still another object of the present invention is to provide a catalytic construct comprising subnanometer clusters in fluid communication with stability enhancing support substrate topographies. A feature of the invention is the isolation of metal clusters from each other on support substrate so as to minimize Oswald ripening, partial evaporation of clusters, and aggregation of clusters during catalytic processes. An advantage of the invention is that original 2 to 4 Angstrom cluster sizes are maintained as a means for assuring contact between all catalyst atoms in each cluster and the reactant to be transformed.

In brief, this invention provides a method for producing a catalyst system, the method comprising forming metal clusters onto a substrate such that all of the atoms forming each of the clusters are under-coordinated; and surrounding each of the clusters with a means for preventing fluid communication between the clusters and sintering of clusters.

Also provided is a method for producing stabilized sub-nanometer catalysts, a method of fabricating sub-nanometer catalysts by size-selected cluster deposition, the preparation and utilization of size-selected silver clusters for epoxidation of propylene, and the preparation and utilization of size-selected gold clusters for the epoxidation of propylene.

BRIEF DESCRIPTION OF THE DRAWING

The foregoing and other objects, aspects and advantages of this invention will be better understood from the following detailed description of the preferred embodiments of the invention with reference to the drawing, in which:

FIGS. 2A-D are a series of schematic diagrams detailing the formation of metal clusters in and around pores of a substrate, in accordance with features of the present invention;

FIG. 3A-D is a pictorial of the activity and selectivity of the invented catalyst system, in accordance with features of the present invention;

FIG. 10 is a schematic of the production of catalytic cluster wells, in accordance with features of the present invention.

DETAILED DESCRIPTION OF THE INVENTION

Figure 1:
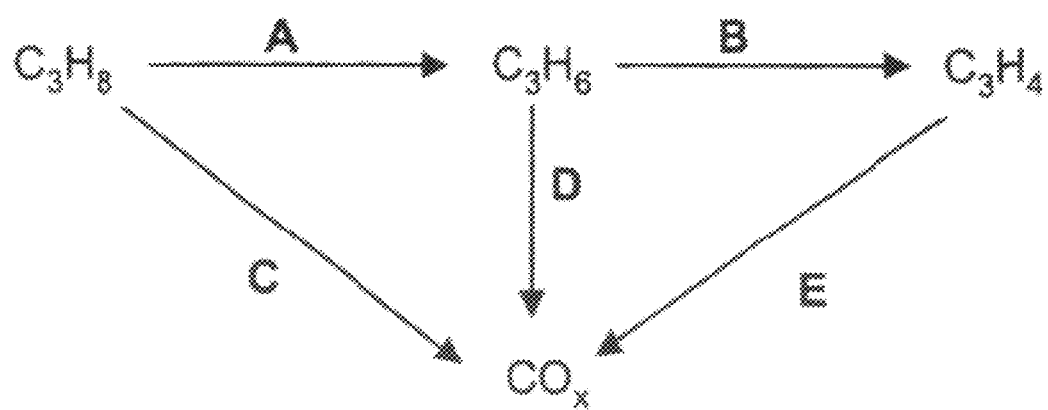
FIG. 1 is a reaction diagram of typical propane oxidative dehydrogenation pathways.

Presented here is a novel application of size-preselected metal-containing clusters under realistic high temperature catalytic conditions. More specifically, the invention produces and utilizes size selected sub-nanometer metal cluster-based catalysts and up to several nm size-selected nanoparticles for chemical conversions such as epoxidation and dehydrogenation.

The invention further enables an atom-by-atom tunable catalytic activity of size-selected clusters supported on technologically relevant oxide surfaces, including single-crystal oxide surfaces, amorphous oxide surfaces, and single-crystal amorphous surfaces. High catalytic activity and selectivity in oxidation reactions of high industrial importance was achieved by using highly monodisperse (i.e., all clusters comprised of the same number of atoms) sub-nm size (i.e., between 0.2 to 1 nm) atomic metal clusters, as well as 1-3 nm size particles. The applied combination of techniques enabled the control of surface composition as well as catalytic particle size and composition—prerequisites for producing highly uniform active sites on technologically relevant supports.

These catalytic properties are the result of geometric and electronic characteristics of the clusters, such as under-coordinated surface atoms. Specifically, the invention provides for size-selected clusters of between 4 and 24 metal atoms, preferably 6-16 metal atoms, and most preferably 8-10 metal atoms. Another embodiment of the invention provides for size-selected clusters of between 4 and 12 metal atoms. These clusters are supported or otherwise stabilized on uniquely shaped support substrates to provide highly active oxidative dehydrogenation catalysts. The catalysts, so positioned, provide a route to bond-specific chemistry with target moieties on feedstock compounds. Either an even number or an odd number of atoms can comprise manufactured clusters.

Subnanometer clusters possess reactivity properties not observed in their bulk analogs, which can make them attractive for catalysts. Subnanometer clusters have a much higher fraction of highly under-coordinated atoms compared to larger nanoclusters. However, experimental studies on sub-nanometer particles at high temperatures (i.e., at and above 500° C., such temperatures typical of industrial catalytic conditions) have been hampered by the inability to stabilize the clusters. At such temperatures, clusters tend to sinter. Sintering in general leads to the formation of large nanoparticles accompanied by change in activity and/or selectivity.

Surprisingly and unexpectedly, the inventors have determined that the clusters are flexible, such that they change shape when interacting with feedstock gases, such as when feedstock gases initially collide or otherwise contact the clusters. In the case of clusters between 0.5 nm and 25 nm in size, the particles change their aspect ratio (width to height ratio) during the reaction when they are exposed to a mixture of reactants. Also, the aspect ratio changes with reaction temperature. For example, the inventors observed that Nanosized 6-25 nm particles usually form oblates on the surface. After adding the reactant at room temperature, they will flatten (i.e., aspect ratio increases) upon the introduction of the reactants. When heated during reaction, they will become taller again (lower aspect ratio). In the case of nanoparticles, that is substantially always a three dimensional 3d change. Sub-nanometer clusters may be planar (2D) and even "stand upright", so as to protrude from the surface. They may undergo a "flip" down along the surfaces. Or, they undergo a two-dimensional to three-dimensional structural isomerization/change. These two dimensional and three dimensional changes confer surface area enlargements to facilitate more efficient conversions.

The inventors devised a process for preventing agglomeration between atom clusters consisting of between 4 and 20 atoms.

The invention provides for partial oxidation catalysts having extremely high selectivities and activities, said selectivities and activities being sustainable, after reaction start up, without having to continually supply energy (e.g. heat) to the reaction system. One embodiment of the invention provides a very high activity of subnanometer Pt-cluster based catalysts for the oxidative dehydrogenation of propane to propylene. Combined with quantum chemical studies, this invention shows that the high activity is due to the under-coordination of the Pt in the clusters and that the clusters favor the scission of C—H bonds relative to C—C or C═C bonds.

The invention further includes techniques for stabilizing size-selected cluster-based catalysts through atomic layer deposition of oxides. The inventors have developed and successfully tested protective over coatings of the catalytic samples with ALD. Using this technique, the clusters were immobilized but still rendered accessible to reactants. The stabilized clusters resisted sintering at temperatures greater than 550° C. while retaining their activity and selectivity. This resiliency was determined from a 30-hour test of catalytic activity. During this duration, no measurable change in catalytic activity and selectivity was noted.

By changing the size of particles in an atom-by-atom fashion, the physical (e.g. optical, shape and morphology) and chemical (e.g catalytic) properties can be tuned to arrive at clusters having specific characteristics. Such fabrication is not possible by using standard methods. The inventors have developed the technique of size-selected cluster deposition which solves this problem and allows fabrication of materials with tunable physical and chemical properties.

For the epoxidation of propylene (one of the highest in industrial importance) one of the most frequent catalysts used is silver based. However the selectivity of those catalysts is very poor. The main cause is due to broad distribution of sizes prepared by classical techniques. The inventors provide a size selected, silver, cluster-based catalyst for the epoxidation of propylene. Specifically, the inventors found that by optimally tuning the monodisperse catalyst size, their activity and selectivity can be altered and optimized.

Also provided are size-selected gold cluster-based catalysts for selective epoxidation of propylene. One embodiment of the invention demonstrates that small gold clusters ($Au_{6-10}$) are highly active for propene epoxidation; thus providing further evidence for the unique catalytic properties of sub-nanometer clusters. An embodiment of this invention is support of 2-5 angstrom diameter clusters (approximately a 10 atom diameter) on alumina. The invented $Au_{6-10}$ catalyst, supported on Alumina, facilitates epoxidation of propane using water additive. As such, the invented catalyst eliminates the need for hydrogen heretofore required to facilitate epoxidation reaction. The epoxidation is further optimized with improving the long-term stability of the gold via a protective ALD overcoat, as discussed infra.

Figure 2A:
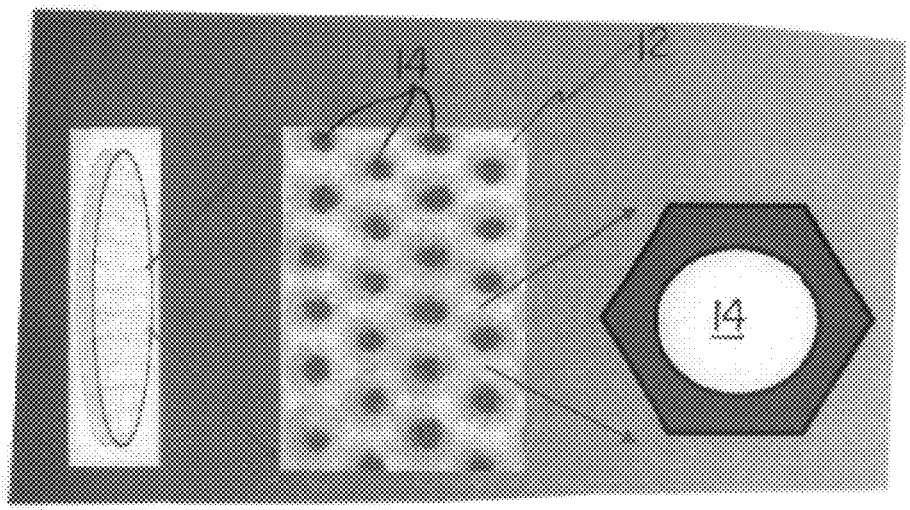

FIGS. 2A-D are schematic diagrams of the preparation of the invented catalyst system designated in FIG. 2D as numeral 10. Generally, the foundation of the system comprises a substrate 12 containing a plurality of pores 14, channels or apertures extending transversely through the substrate, so as to have a first end (mouth end) and a second end (exit end). In this flow-through configuration, these pores serve as transverse channel reaction-ways, apertures, or conduits. An exemplary constituent of the substrate 12 is a mesoporous substrate (i.e., a material containing pores with diameters between 2 and 50 nanometers), such as anodized aluminum oxide (AAO). Other suitable foundation substrates include oxides with pore structures similar to AAO, mesoporous silica, or zeolites after their pore diameters are modified via the invented pore constriction method. Mesoporous silica has larger pore (1-30 nm) and is suitable to ALD pore tuning followed by application of the invented clusters.

The inventors found that the porosity of the substrate provides a means for maintaining the stability of the clusters over a temperature range of 20° C. to 400° C. The high surface area of the pores provides large areas to support high dispersion of particle—(i.e., large distances between the clusters. Also, the high surface area provides large numbers of defect/binding sites the clusters can strongly bind to and not move/sinter. Pore diameter: may provide additional tuning parameter for increased selectivity due spatial constraints on reactants and products. A feature of this invented paradigm is that the diameter of the clusters is much smaller than the diameter of the pores. This steric hinderance conferred by the catalyst support provides stability to the cluster.

Surprisingly and unexpectedly, the inventors found that surface defects in the supporting oxide provide a means for stabilizing the clusters and in modifying their charge state. Such defects include oxygen vacancies on the lattices of support oxides. Such conversions are observed to occur at low temperatures compared to conversions instigated by clusters residing on defect-free oxide surfaces.

Figure 2B:
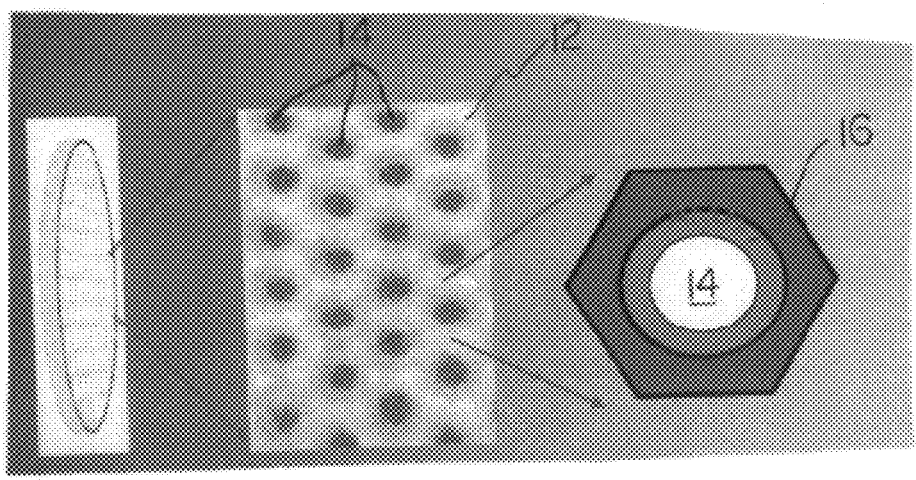

Covering at least substantial surfaces of the substrate is a means for facilitating adherence of active metal to the substrate, and a means for optimizing the pore structure of the underlayment. Such adherence-promoting means include an alumina layer 16, as depicted in FIG. 2B. The adherence-promoting layer 16 covers the surfaces defining at least a substantial number of the pores 14, such that the openings of these pores, along with the internally extending surfaces of the pores, are lined by the adherence promoting layer.

Figure 2C:
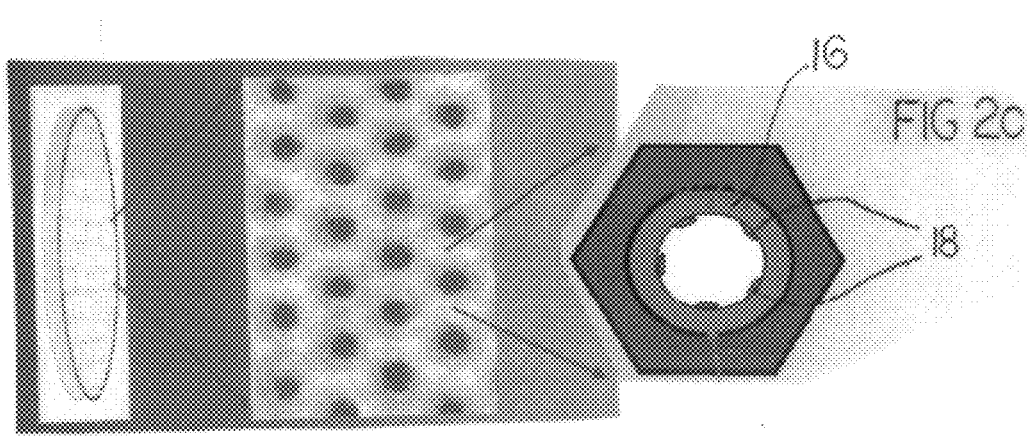

Once the adhering promotion layer 16 is deposited, catalyst clusters 18 are deposited on the promoting layer 16, as depicted in FIG. 2C. As described infra, placement of the catalysts on and about the pores are predetermined, depending on the activity of the final construct 10 desired. For example, clusters arranged at a first opening (i.e., the mouth rim of a pore so defined by the surface of the substrate 12 facing the direction from which reactants are flowing) will impart a different catalytic effect than clusters arranged at a second opening of the pore (i.e, the exit rim so defined by the surface of the substrate facing away from the source of reactant flow).

Clusters deposited directly at the pore openings, and onto longitudinally-extending interior surfaces of the pores (i.e., the surfaces located inside of the substrate, between the entrance and exit openings of the pores) defines a first catalytic reaction zone. These clusters vary in height and protrude, or otherwise extend medially, toward the longitudinal axis of the pore at a distance of between 0.20 nm to 1. nm. Preferably the clusters reach a height ranging from about 0.3 to 0.6 nm, and most preferably a height of 0.5 nm. These inward projecting clusters, and similarly arranged clusters projecting from opposing surfaces of the pores, provide a sieve to allow only certain sized molecules (between 2 and 180 Angstroms) to pass. Clusters in this first reaction zone provide conversions at between 400° C. and 600° C.

A considerable fraction of clusters remains on exterior or outside surfaces of the substrate not containing pores, therefore defining a second reaction zone. Cluster sizes in this second reaction zone are generally greater than 1 nm. (One embodiment of the invention comprises cluster sizes in this second reaction zone of approximately 2 nm in diameter.) Inasmuch as this fraction is not reactive at the mild reaction conditions of as low as 400° C., due to the large sizes of the clusters residing there, this fraction provides a means for providing additional reaction capacity at higher temperatures. Such higher reaction temperatures are selected above 400° C., generally between 600 to 1000° C., preferably between 600-700° C., and most preferably at 650° C.

The cluster fractions could be comprised of different catalyst materials to confer a single multi-functional catalytic surface. Alternatively, different cluster fractions could populate different reaction zones, as defined above, to provide a plurality of catalytic surfaces on the same substrate, each surface specific for a different reaction.

In an embodiment of the invention discussed infra, and depicted in FIG. 2D, intermediate the clusters 18 is positioned a means for preventing fluid communication between clusters, such means being a film 19. The film 19 is arranged such that each of the clusters are physically surrounded by the film. In an embodiment of the invention, portions of the substrate remain uncovered from the film. Generally, the film is deposited after the clusters are formed on the adherence-promoting surface 16, and to a height of at least 10 percent, and usually from 20 to 70 percent of the height of the clusters. More typical film thicknesses between clusters are 30-60 percent of the height of the clusters. A preferable thickness is about 50 percent of the height of the clusters.

In one embodiment of the invention, anodized aluminum oxide (AAO) foundation substrates are used. These AAO membranes are fabricated by electrochemically etching aluminum metal and possess a high density of ordered nanopores with typical pore diameters of 40 nm and pore lengths of 70 microns. Pore lengths can vary and generally are from 30-120 microns, and more specifically from 50-100 microns. This provides the oxide layer underlayment necessary to ensure adhesion of the subsequently formed alumina layer, the latter of which provides a chemically-uniform surface. The AAO membranes are subsequently coated using ALD with a conformal layer of material such as alumina to shrink the pore diameters and to provide a chemically uniform surface.

While a myriad of pore diameters exist on such substrates, final pore diameters above 8 nm, and preferably approximately 10 nm, are fabricated by coating the substrate with alumina film using ALD. These 8 nm pore diameters are large enough to prevent clogging during any catalytic process. Pore diameters greater than 500 nm should be avoided, otherwise, fluid transport through the pores will be too rapid for complete chemical conversion during the catalytic process.

Flipping the AAO substrate downstream of the sputtering ion source will enable deposition of catalytically active clusters at both the entrance and the exit of the pores. Positioning the same metal at both ends provides a means for enhancing catalytic efficiency. Alternatively, have a first metal at one end and a second metal at the other end provides a multifunctional catalyst. For example, positioning platinum catalyst clusters at an upstream end produces propylene from a propane feedstream. If gold clusters are situated at a downstream end, propylene oxide is formed from the just produced propylene.

In one embodiment of the invention, specifically sized clusters are formed in gas phase and those clusters are vectored to portions of the adherence promoting layer 16. Such vectoring means includes, but is not limited to, establishing a voltage between the cluster formation device and the adherence promoting layer, imparting kinetic energy to the clusters and directing those clusters to the adherence promoting layer via magnetic or electric fields, the application of a pressure gradient, and combinations thereof.

Generally, the cluster vector is perpendicular to the surface onto which the adherence promoting layer is formed. Those clusters traveling toward the membrane and coaxially with the longitudinal axis of the pores 14 will ultimately deposit at the mouths of those pores and within those pores to form the first reaction zone discussed supra. Those clusters directed toward the membrane but not in line with the pores will deposit elsewhere on the surface of the membrane and either be of the same size of the clusters confined by the pores, or else of a larger size. Such larger size pores depositing outside of the pore and away from areas in close spatial relationship with the pore openings will constitute a second reaction zone, as discussed supra.

Catalyst Support
Preparation Detail

As noted supra, sintering of catalysts under reaction conditions can lead to the loss of highly size-dependent catalytic activity and selectivity. The inventors solved this problem by proper choice of the material and morphology of the support. Technologically relevant support materials include AAO membranes, oxides and other surfaces. Exemplary support materials include AAO membranes. A suitable embodiment of these membranes are disc-shaped having up to $10^{11}$ pores per square centimeter. Each pore or reaction-way has a diameter of between 10 and 20 nanometers and runs completely through the substrate so as to provide fluid communication between the oppositely facing surfaces of the substrate. Such substrate serves as an ideal model of monolith-based supports used by industry, including catalytic converters in automobiles.

Figure 6:
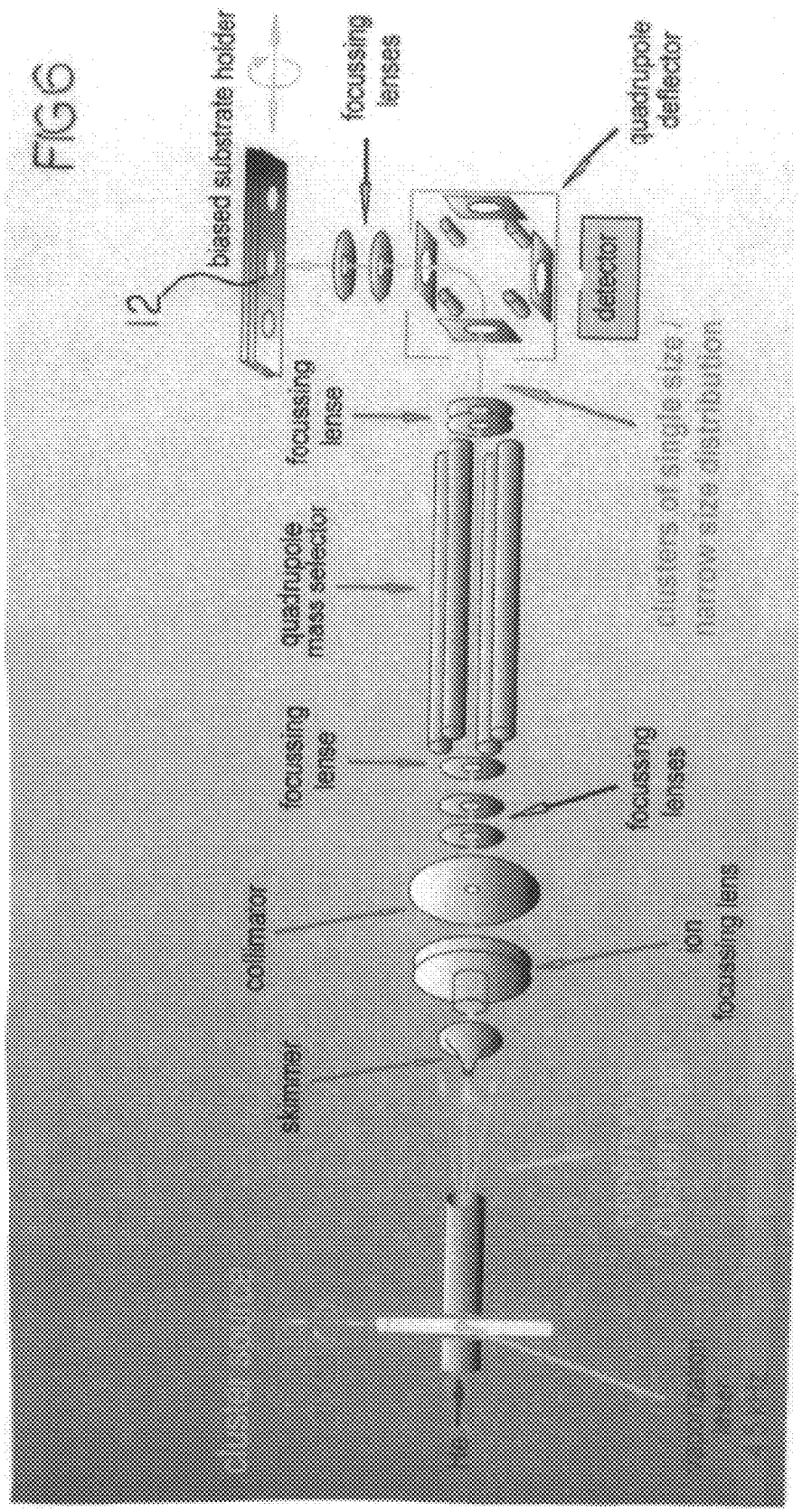
FIG. 6 is a schematic diagram of a cluster forming device, in accordance with features of the present invention.

While a disc configuration is illustrated in FIG. 2A-D, other three dimensional substrates also can be utilized, including cylinders, spheres, cones, frustoconical surfaces, and combinations thereof. Also, while the substrate is depicted in FIG. 6 as mounted in a stationary position, gimbal mounting or fluidized bed applications are also envisioned so as to optimize exposure of reactant molecules to cluster atoms from every angle of incidence.

The inventors' studies showed that small platinum clusters are exceptionally stable on thin alumina films fabricated by atomic layer deposition (ALD). These films were selected to pre-coat the foundation substrate (such as anodized aluminum oxide (AAO) membranes and membranes comprised of flat silicon wafers) prior to cluster deposition. The aforementioned AAO membranes are commercially available, for example as Whatman Anodisc 13 available through Whatman Inc. (Piscataway, N.J.).

Prior to coating with alumina, the foundation substrates have a thickness of 60 μm, and consist of a support layer comprised of 200 nm diameter pores followed by a 4 μm separation layer with 20 nm diameter pores. This four micron separation layer is the oxide layer as part of the original AAO substrate. By coating the membranes with $Al_2O_3$, their pore diameters were reduced to 10 nm.

In an embodiment of the invented substrate, and as noted supra, on top of the alumina layer and in between the individual clusters 18 is deposited a metal oxide film 19. Suitable oxides include tin oxide, titanium oxide, zinc oxide, a second layer of aluminum oxide, and combinations thereof. This film is provided to stymie sintering of the clusters, fluid communication between the clusters, and cracking of the feedstock.

In one embodiment, ten cycles of tin oxide ALD were performed to deposit a 0.3 nm film. The tin oxide deposition was performed using alternating exposures to tin tetrachloride ($SnCl_4$) and deionized water at deposition temperatures of 400° C. More details of tin oxide deposition is found at "Subnanometer Platinum Clusters as Highly Active and Selective Catalysts for the Oxidative Dehydrogenation of Propane"

S. Vajda, M. J. Pellin, J. P. Greeley, C. L. Marshall, L. A. Curtiss, G. A. Ballentine, J. W. Elam, S. Catillon-Mucherie, P. C. Redfern, F. Mehmood and P. Zapol, Nature Materials 8, 213 (2009) and Viirola, H., Thin Solid Films, 249, (1994), 144-149, the entirety of which are incorporated by reference.

In one embodiment of the invention, a suitable oxide layer 19 thickness is one which does not exceed the height of the cluster so as to stymie contact of reactant molecules to the atoms comprising the cluster. As such, film thicknesses of up to 0.5 nm are typical. (The heights of typical clusters range from about 0.3 to 1 nm, and preferably 0.3 to 0.7 nm.

However, in another embodiment of the invention, clusters reside in wells or depressions defined by the film. In this embodiment, an organic protective cover 21 is placed over the clusters, prior to deposition of the film 19. Then, the film 19 is applied to the entire surface supporting the clusters, without overcoating the clusters. After a predetermined thickness of film is applied, the surface resembles a snow-covered rock pile, with "bumps" in the covering film indicating cluster location. A means for removing the protective cover over the cluster is utilized to form individual but nested clusters, as depicted in FIGS. 10 A-D.

For instance, in the case of protecting gold clusters, the protective cover 21 consists of an alkane thiol such as dodecanethiol that can be applied selectively to bond only to the gold clusters and not to the surrounding substrate. This application is effected by either using vapor deposition of the dodecanethiol or from a solution of dodecanethiol in an organic solvent such as hexane. Next, ALD is performed to deposit for instance a metal oxide layer such as $TiO_2$, $Al_2O_3$, or ZnO using alternating exposures to $TiCl_4/H_2O$, $Al(CH_3)_3/H_2O$, or $Zn(CH_2CH_3)_2/H_2O$, respectively. The number of ALD cycle is adjusted to control the thickness of the metal oxide layer. The metal oxide layer will only grow on the surrounding support surface that is covered by the necessary hydroxyl functional groups to promote the ALD film growth, but not the cluster which is protected by the dodecane thiol organic layer. Finally, the dodecane thiol layer is removed by heating the sample in oxygen or ozone to burn away the alkane thiol.

Cluster Formation Detail

While emphasis is being placed on the use of platinum as a catalyst metal species, other metals, including gold, silver, palladium, cobalt, nickel, and combinations thereof, also are suitable.

An embodiment of the catalytic surface was produced as follows: A continuous beam of metal clusters was generated in a high-flux laser vaporization cluster source, as depicted in FIG. 6. In a laser vaporization source, metal is evaporated by an intense laser. The produced clusters expand in helium carrier gas to the vacuum and enter a mass filter setup. In the mass filter setup, narrow distributions of catalytic cluster sizes are produced. For example, narrow cluster distributions in the size range $Pt_{n+}$, n=1, . . . 10, with two to four dominant sizes were produced. It is noteworthy that the number of atoms comprising the cluster in vapor phase is the same number comprising the cluster in solid phase even after deposition on the membrane. The stabilizing effects of the support surface (in one embodiment the alumina surface) is responsible for this atom number consistency.

The clusters emerging form the continuous beam cluster source possess identical velocity. Due to the variation in their kinetic energy with size, in addition to the single mass selection on a quadrupole mass filter, narrow distributions of clusters with one to four sizes can be isolated utilizing a quadrupole deflector operated in energy filter mode.

The kinetic energy of clusters landing on the surface is controlled by biasing the substrate to a desired voltage. Low deposition energies are used to avoid possible fragmentation of clusters upon their impact on the surface. The flux of $Pt_{8-10}$ clusters landing on the support was monitored in real-time using a pico-ampere meter. By integrating the accumulated charge of the positively charged $Pt_{8-10}$ clusters landing on the surface, the exact surface coverage with Pt-metal is determined.

With such biased substrates, typical deposition energies are on the order of 0.5 eV/atom or less with the goal to avoid cluster fragmentation upon impact. Average deposition currents are in the order of tens to several hundreds of picoamperes (pA), depending on the size of clusters and higher conversion rates. Preferable deposition currents are between 100 and 2000 pA.

Biased substrates provides an exact determination of the metal coverage/loading applied of the cluster sizes settling onto the support substrate (i.e., same number of atoms) as those clusters formed during their initial gas phase production.

Since only 10.5% of the facing area of the membrane was exposed to clusters, and to the propane feed, a multiplication factor of 9.5 is applied to obtain the corrected propane conversion rate on the Pt-cluster coated fraction of the AAO membrane. By calculating the relative pore opening area to the total surface area of the membrane, 28% of the $Pt_{8-10}$ particles, corresponding to 252 ng of Pt-metal, enter the pores. The rest forms metallic platinum on the face of the AAO membrane as confirmed by XPS. Thus, 252 ng of Pt was used for the calculation of the turnover frequencies.

In order to increase the substrate surface area covered by clusters, the substrate is translated or moved during deposition, analogous to moving a backstop. All samples were prepared using the identical scheme, surface coverage and cluster size distributions consisting of $Pt_{8-10}$. A loading of the supporting AAO membrane having a 13 mm diameter was made, with a total amount of Pt metal deposited being a few hundred nanograms, preferably between 100 nanograms (ng) and 500 nanograms, and most preferably about 300 nanograms per approximately 0.5 $cm^2$ area.

The Pt cluster forms Pt—O bonds with the surface, resulting in significant charge transfer to the cluster. The binding of the cluster to the surface (~3 eV) is consistent with the stability of the subnanometer Pt8 clusters on alumina, but does not significantly affect the cluster's chemical reactivity. The inventors investigated the stability of a positively charged Pt8 cluster on alumina and found that it withdraws electrons from the surface of the foundation substrate and becomes negatively charged.

Further details of the size selected cluster deposition device which provides a means for cluster soft landing and controlled surface coverage of clusters on a target substrate can be found in Vajda et al. Nature Materials, DOI:10.1038/NMAT2384, Feb. 8, 2009, and incorporated herein by reference in its entirety. Briefly, that reference discloses that a continuous beam of platinum metal clusters is generated in a laser vaporization cluster source which utilizes a Nd:YAG laser operating at 4.5 kHz. The beam of neutral and charged platinum clusters passes through a biased skimmer into the ion guide of the second differentially pumped vacuum stage and then into the third vacuum stage. The positively charged clusters are then guided and focused into the quadrupole mass spectrometer for analysis. Narrow Pt-cluster distributions) in the mass range of up to 2000 amu can be produced by optimizing the temperature of the clusters source, pressure of the helium carrier gas and potential settings on the individual ion optics elements.

After the mass analysis of the cluster distribution is completed, by reversing the polarity settings on the quadrupole deflector, the mass-selected Pt-clusters are deflected into an ion lens setup placed in front of the substrate. The substrate (a flat oxide surface or an AAO membrane) is mounted on a translation stage. By translating the support during cluster deposition, a larger area of the support can be covered by the catalytic clusters. Clusters of single size can be deposited by operating the quadrupole mass filter in a mass resolving mode. Alternatively, the quadrupole can be operated in ion-guide mode—guiding the narrow cluster size distribution towards the quadrupole deflector Using this approach, very narrow distribution of cluster sizes can be extracted from the beam when using the deflector as an energy filter (e.g. 2 to 4 dominant cluster sizes). $Pt_{8-10}$ clusters were soft-landed on AAO membranes.

This procedure resulted in the formation of metal clusters comprised of surface atoms only (i.e., no internal atoms) such that each individual atom serves as a catalytic site by being physically exposed to the reaction environment so as to facilitate unhindered fluid communication between the atom and the target reactants. In one embodiment, the invented substrate enables these particles to be located on one side of the membrane only, thus providing a one-sided, three dimensional matrix of microreactors, the entire matrix being 12 millimeters in diameter. In this embodiment, each of the microreactors comprises a pore about 10 nm in diameter, each pore containing a limited number of highly dispersed Pt particles along its opening and on its interior surfaces. The clusters ranged in height from 3 to 5 Angstroms.

Silver-, Gold-Induced Epoxidation Detail

Separately, the inventors have shown for the first time that epoxidation of propylene is feasible on alumina supported sub-nanometer size selected gold catalysts, and that the long term stability of the clusters is improved by a protective ALD overcoat. The protection of the gold clusters by an atomic layer deposition of alumina or some other protective overcoat will reduce sintering and prevent an increase in cluster size over a period of time while operating in a hot (more than 500° C.) environment.

The same deposition detail as described above for Pt clusters was used to deposit size-selected gold ($Au_{6-10}$, wherein the subscripts designate the number of atoms per cluster) and silver $Ag_3$ clusters and 6-25 nm size clusters on flat $Al_2O_3$/$SiO_2$/Si supports. In the case of gold clusters, surface coverages in the order of 3% of atomic monolayer (ML) equivalents were applied. In the case of silver clusters, coverages of up to 5% ML were used The inventors have demonstrated that by optimally tuning the monodisperse catalyst size, catalyst activity and selectivity can be altered and optimized. This is particularly relevant when silver clusters are produced and utilized to facilitate the epoxidation of propylene to propylene oxide. Propylene oxide is used for making polyurethane, unsaturated resins, surfactants and other products.

The continuous beam of metal atoms for deposition is generated in a high-flux laser ablation cluster source which utilizes the frequency doubled (532) output of a Quantronix Nd YAG operating at 4.5 kHz. During the ablation process, neutral as well as positively and negatively charged toms and their aggregates are formed. Narrow cluster distributions in the size range $Ag_n^+$, n=1, . . . 10, with two to four dominant sizes can be produced by optimizing the temperature of the clusters source, the pressure of the helium gas carrier in the cluster source, and potential settings on the individual ion optics elements of the beam line. In one embodiment, an optimal helium pressure is 20 Torr, with temperatures of about 20° C.

The aforementioned silver and gold cluster based nanocatalysts are prepared in the same manner and with the same equipment as the platinum clusters, as described supra.

Overcoat
Detail

An embodiment of the invention utilizes a protective overcoating of the catalytic particles. Atomic layer deposition is one means for applying the overcoat. Using this technique, the clusters are immobilized but still accessible to the reactants. In this regard, only a small portion, i.e., only the periphery in some instances, of the clusters actually contact the overcoat, so as to assure maximum fluid communication between the atoms in the clusters and the target reactant molecules. Preferably, the overcoating resides between the clusters to serve as a barrier against the clusters migrating toward each other and agglomerating.

The overcoating technique utilizes a sub-monolayer of oxide film (e.g. SnO, $Al_2O_3$, $TiO_2$). Such overcoatings suppress sintering of catalysts and decrease cracking of the feedstock material (e.g., propane) at elevated temperatures required for high-temperature oxidative dehydrogenation.

For example, a tin oxide overcoating was produced to optimize and otherwise promote the functionality of the invented platinum-based catalysts. The oxide was applied via ALD. Tin oxide ALD was performed using alternating exposures to tin tetrachloride ($SnCl_4$) and deionized water at deposition temperatures of 400° C. Ten cycles of tin oxide ALD were performed using 2 second reactant exposures and 5 second purges between exposures to deposit a 0.3 nm film.

Given current ALD capabilities, effective film thicknesses are 0.5 nm or greater. However, from a chemistry standpoint, any thickness which yields an oxide concentration in close spatial relation and in fluid communication with catalytic clusters capable of imparting anti-sinter, anti-cracking characteristics to the catalyst cluster is suitable. Therefore, this disclosure should not relegate the effectiveness of the overcoat to current ALD limitations, as other deposition techniques are also suitable to impart suitable oxide concentrations. For example, the inventors found good antisintering protection in overcoats comprised of about 0.3 nm thick oxide films.

Catalyst
Test Details

Figure 7:
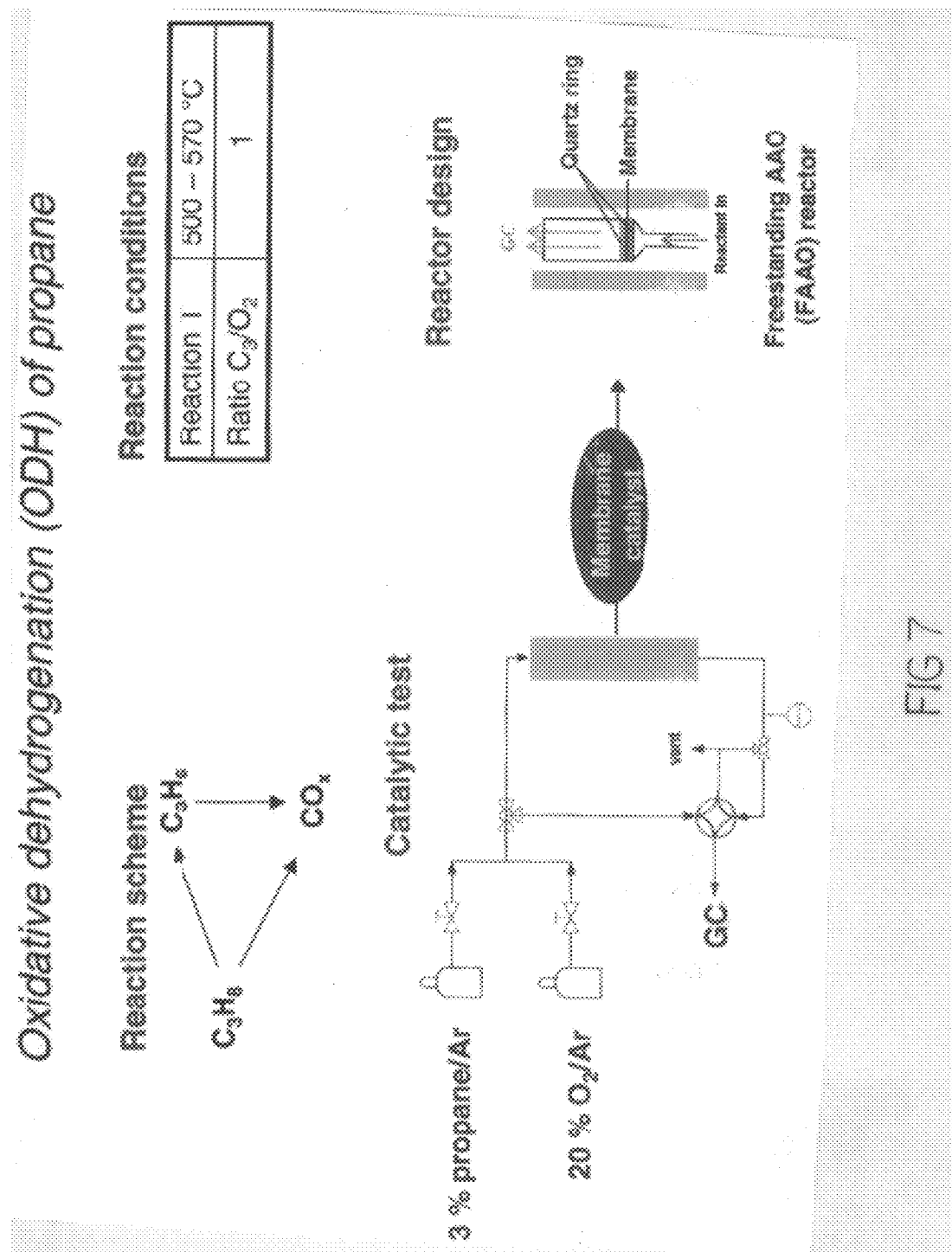
FIG. 7 is a schematic diagram of the reaction scheme juxtaposed to the catalytic test schematic and actual reactor design, in accordance with features of the present invention.

Oxidative dehydrogenation of propane using platinum-based clusters was performed under atmospheric pressure at temperatures up to about 550° C., and normally between 400 to 550° C., in a commercial freestanding AAO flow reactor, such as that depicted in FIG. 7.

Catalyst tests were performed under atmospheric pressure in a flow reactor by employing 10 sccm (standard centimeter cube per minute) total flow of reactants in inert gas, such as argon.

An upper temperature limit of 550° C. was chosen in order to have a direct comparison with the performance of the VOx/AAO catalysts routinely tested in this temperature range. The selection of the 3% propane/Ar mixture, and the 20% O2/Ar mixture is for convenience. Other mixtures consistent with the objectives of the invention are also suitable.

Figure 8:
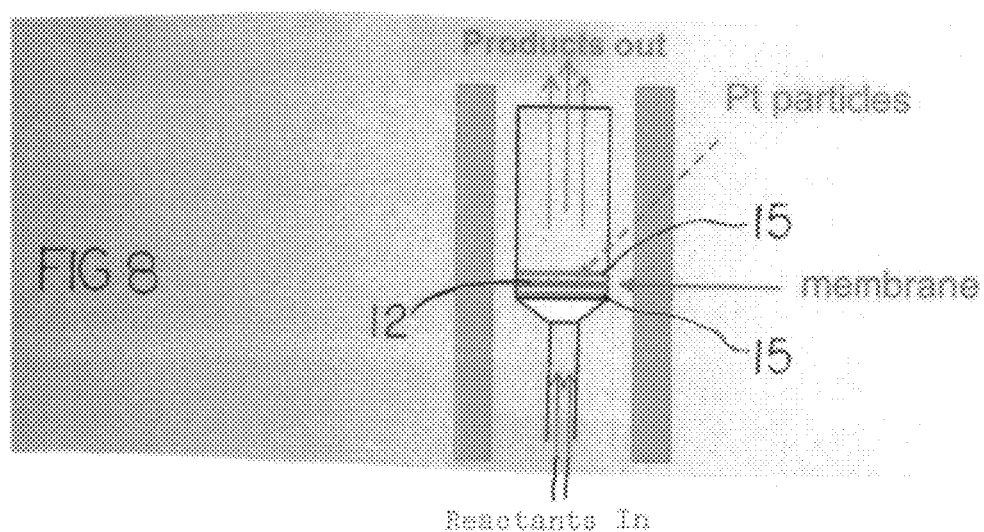
FIG. 8 is an enlarged schematic of the freestanding AAO reactor, in accordance with features of the present invention.

FIG. 8 is a detailed depiction of the freestanding AAO reactor illustrated in FIG. 7. FIG. 8 shows the membrane 12 sandwiched between two quartz rings 15. The rings provide a means to confer rigidity and protection to the membrane.

Reaction products were analyzed downstream of the freestanding AAO reactor by in line gas chromatography, as depicted in FIG. 8. FIG. 8 schematically depicts catalyst (Pt-based catalyst is depicted) deposition on the downstream (i.e. exit) end of the pores of the membrane. This localized loading assures shorter contact times (compared to the shorter contact times which would occur between reactants and clusters loaded at the upstream pore openings). Also, exit pore loading substantially eliminates recontact of product moieties with the clusters inasmuch as such recontact would be against the flow of the process. Fluid flow is depicted by the arrows in FIG. 8. These shorter contact times result in fewer additional reactions occurring. This leads to increased selectivity and lower conversion.

Gold and silver catalysts were utilized in alkene conversions. The catalysts were tested under alkene oxidation conditions at the Advanced Photon Source at Argonne National Laboratory, Argonne, Ill. at atmospheric pressure. Simultaneous mass-spectroscopy detection of products and in situ acquisition of grazing incidence small angle X-ray scattering (GISAXS) images was achieved, while ramping the temperature up to 350° C.

Invented Catalyst Activities/Selectivities
Compared to State of the Art Values

FIG. 3 depicts the activities and selectivities of the invented $Pt_{8-10}$ catalytic systems at temperatures ranging from 400 to 550° C. versus typical ODH catalytic systems. It is noteworthy that Turn Over Frequencies (TOF), or the number of propene molecules formed per metal atom, of the invented system is shown to be 40 to 100 times higher than that seen with the typical vanadium based, or platinum based catalysts, particularly at 400° C. For example, TOF for the invented system ranged from 0.8 per second (at 400° C.) to 2.9 per second (at 550° C.) of propylene molecule produced per Pt atom. The TOFs observed with the invented catalytic surface construct are 40 times that of typical platinum systems and 100 times the TOF exhibited in state of the art vanadium-based systems.

For a uniform comparison with reported catalysts, the TOF was calculated as the number of propylene molecules produced per Pt atom per time unit (seconds) as follows:

a. Determination of the total amount of deposited metal. During cluster deposition, the flux of positively charged clusters reaching the AAO surface is monitored by using a pico-ampermeter. In the knowledge of the cluster size, the over time accumulated charge is used to calculate the number of Pt atoms (and the total mass of Pt).

b. Determination of the fraction of Pt metal landing in the channels of the AAO membrane. The surface plates of the AAO membranes used were imaged by SEM and the area fraction of the channel openings was determined.

c. At the high level of applied coverage of the surface with clusters calculated from the deposition flux data per flat surface area and known from own earlier deposition experiments on flat surfaces, aggregation of the originally small Pt clusters on the front surface of the membrane into large nanoparticles and films was expected. XPS confirmed the presence of metallic platinum on the front surface of the membrane. It is known from literature, that Pt films/surfaces are not reactive under our relatively mild conditions or primarily cause cracking of the feedstock in films and large nanoparticles.

d. Based on the above, for the calculation of the turn-over frequencies of the $Pt_{8-10}$/AAO catalysts, the amount of Pt metal directly landing in the AAO channels was taken into consideration.

In FIG. 3A, the data show an 83.7 percent selectivity when an $SnO/Al_2O_3$ catalyst system is run at 400° C., using clusters, each cluster containing between 8 and 12 platinum atoms. In an embodiment of the invention, the clusters are "neat" in composition, which is to say that substantially every atom in the cluster consists of a single element. This undoped feature provides the means for superior reactivities and selectivities provided by the invented clusters. FIG. 3B depicts a 64 percent selectivity for Propylene when the $SnO/Al_2O_3$ catalyst system is run at 500° C. FIG. 3C depicts a 68 percent selectivity for Propylene when just an $Al_2O_3$ containing substrate is utilized at 550° C.

FIG. 3D depicts the turn-over frequencies of propene produced no the $Pt_{8-10}$ catalysts versus the reference ODH catalysts. Reference catalysts used include those disclosed in Argyle, M. D., Chen, K., Bell, A. T. & Iglesia, E., Effect of Catalyst Structure on Oxidative Dehydrogenation of Ethane and Propane on Alumina-Supported Vanadia. *J. Catal.* 208, 139 (2002); and Silberova, B., Fathi, M. & Holmen, A., Oxidative dehydrogenation of ethane and propane at short contact time. *Appl. Catal. A: General* 276, 17 (2004), all of these references incorporated herein by reference. Turn-over frequency is expressed as the number of propene molecules formed per catalyst metal atom.

The observed product distribution, favoring propylene formation over COx at 400° C. indicates that C—H cleavage by the platinum clusters is more favored than C—C or C=C cleavage.

The product distribution (FIG. 3) indicates that selectivity for propylene over the formation of carbon oxide species is also achieved. The total conversion approaches 25±4% at high temperatures.

The calculated selectivity trends can be understood from the electronic structures of the C—C and C—H bond-breaking transition states. The larger barriers observed for C—C vs. C—H bond breaking are likely due to the $sp_3$ directionality of the orbitals on C compared to the spherical nature of the orbital on hydrogen, which results in poorer overlap between the adsorbate and the reaction site orbitals in the transition state for breaking the C—C bond compared to that for the C—H bond.

Figure 4A:
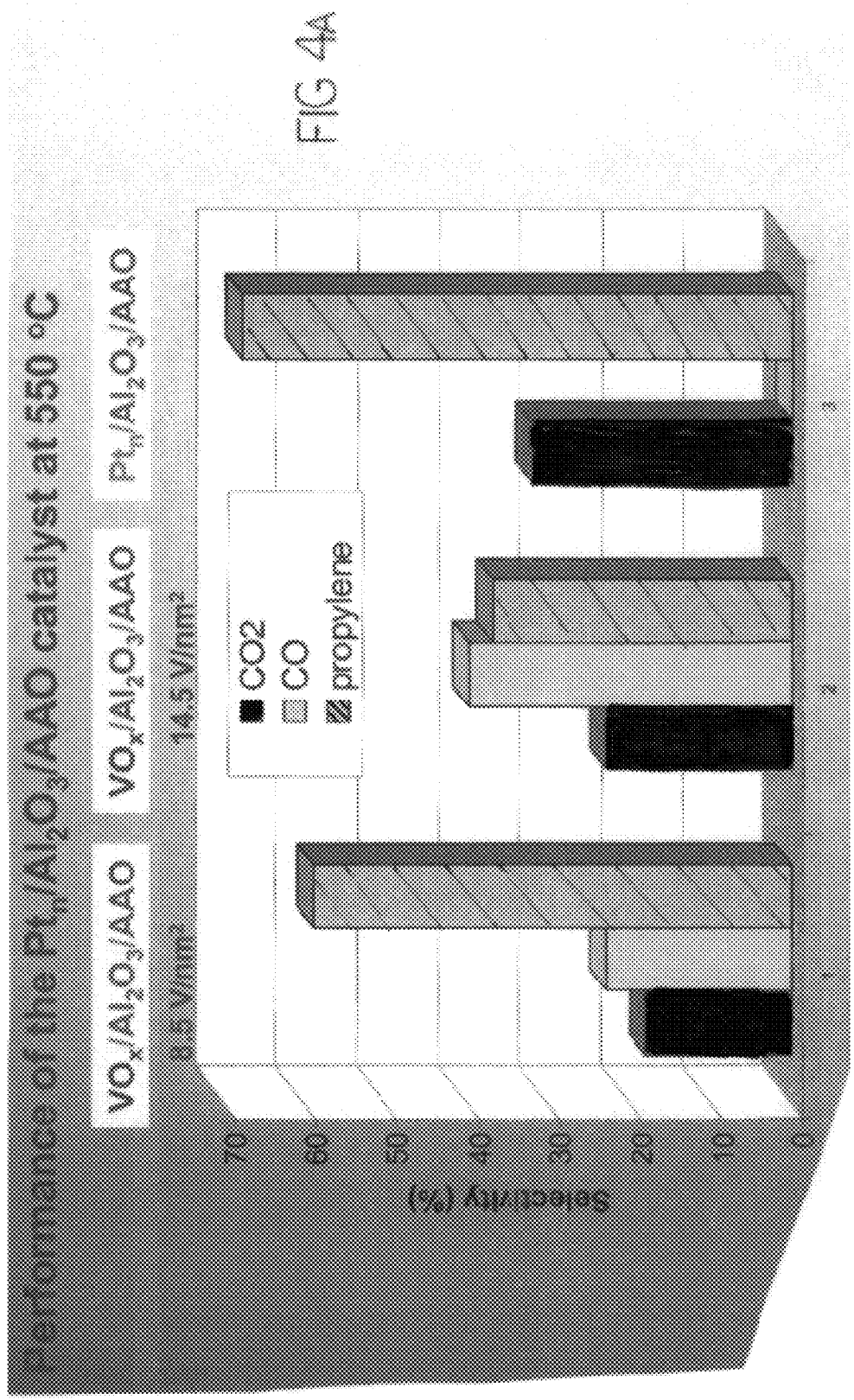
FIGS. 4A-4C is a graphical comparison of the invented catalyst reactivities and selectivities to state of the art catalysts, in accordance with features of the present invention.

Oxidative Dehydrogenation of Propane (ODHP) by $Pt_{8-10}/Al_2O_3$/AAO Catalysts The tests were performed at 550° C. and the performance of the Pt-based catalyst was compared with two reference $VOx/Al_2O_3$/AAO catalysts prepared with different V-loadings (FIG. 4A). The conversion of propane to propene (about 30%) was 3 times higher on the $Pt_{8-10}/Al_2O_3$/AAO catalyst, the per metal atom turn-over frequencies were up to ~100 times higher than on VOx. Moreover, as noted in the third column of FIG. 4A, the selectivity of the Pt-based catalyst was the highest of all catalysts, having $CO_2$ as the single by-product. The extremely high activity can be explained by the extraordinary high reactivity of platinum particles in the smallest size-regime, where practically each every atom of the catalyst particle is a surface atom, thus readily accessible to the reactants.

Oxidative Dehydrogenation of Propane (ODHP) by $Pt_{8-10}/SnO/Al_2O_3$/AAO Catalysts.

Figure 4B:
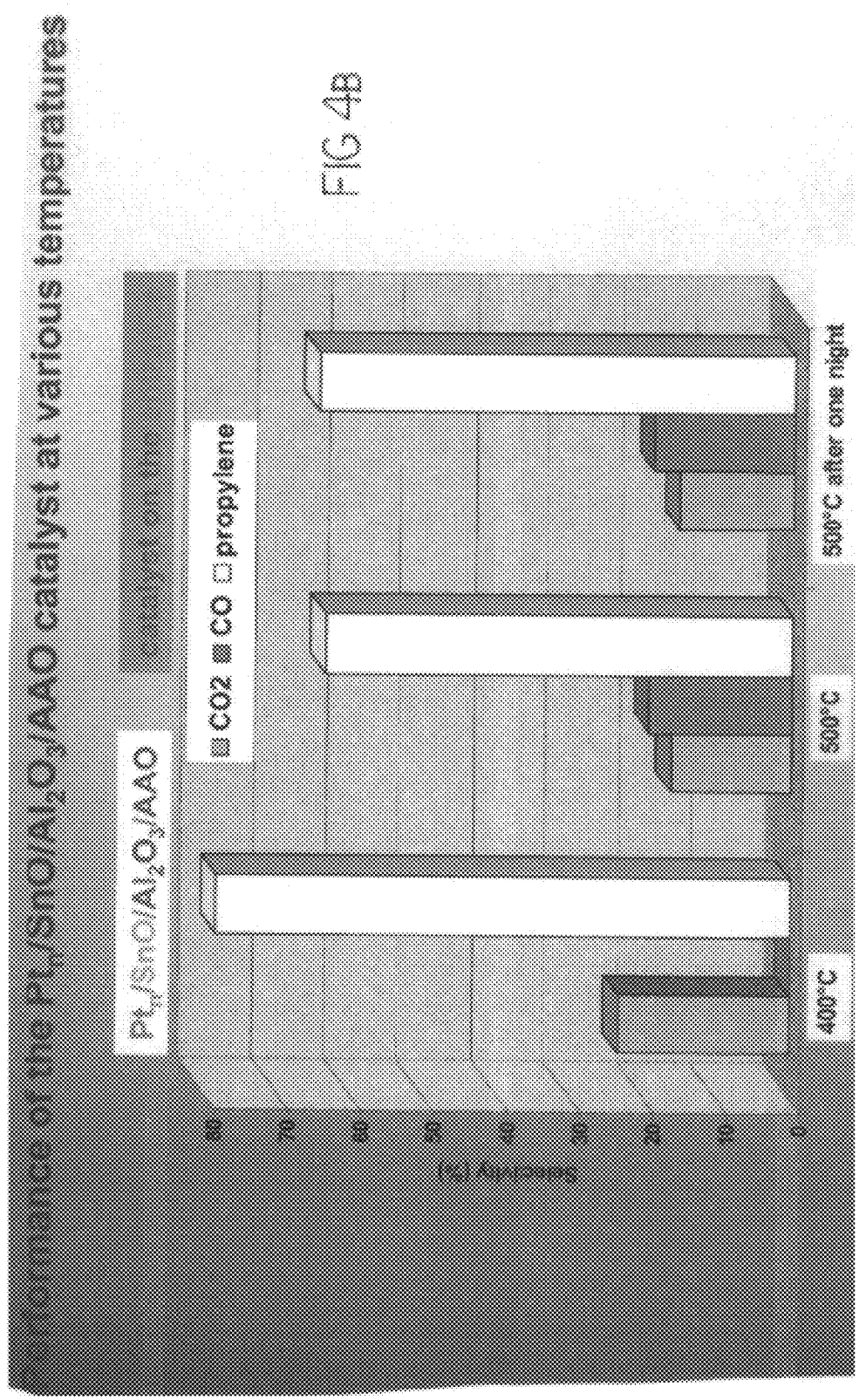
Figure 4C:
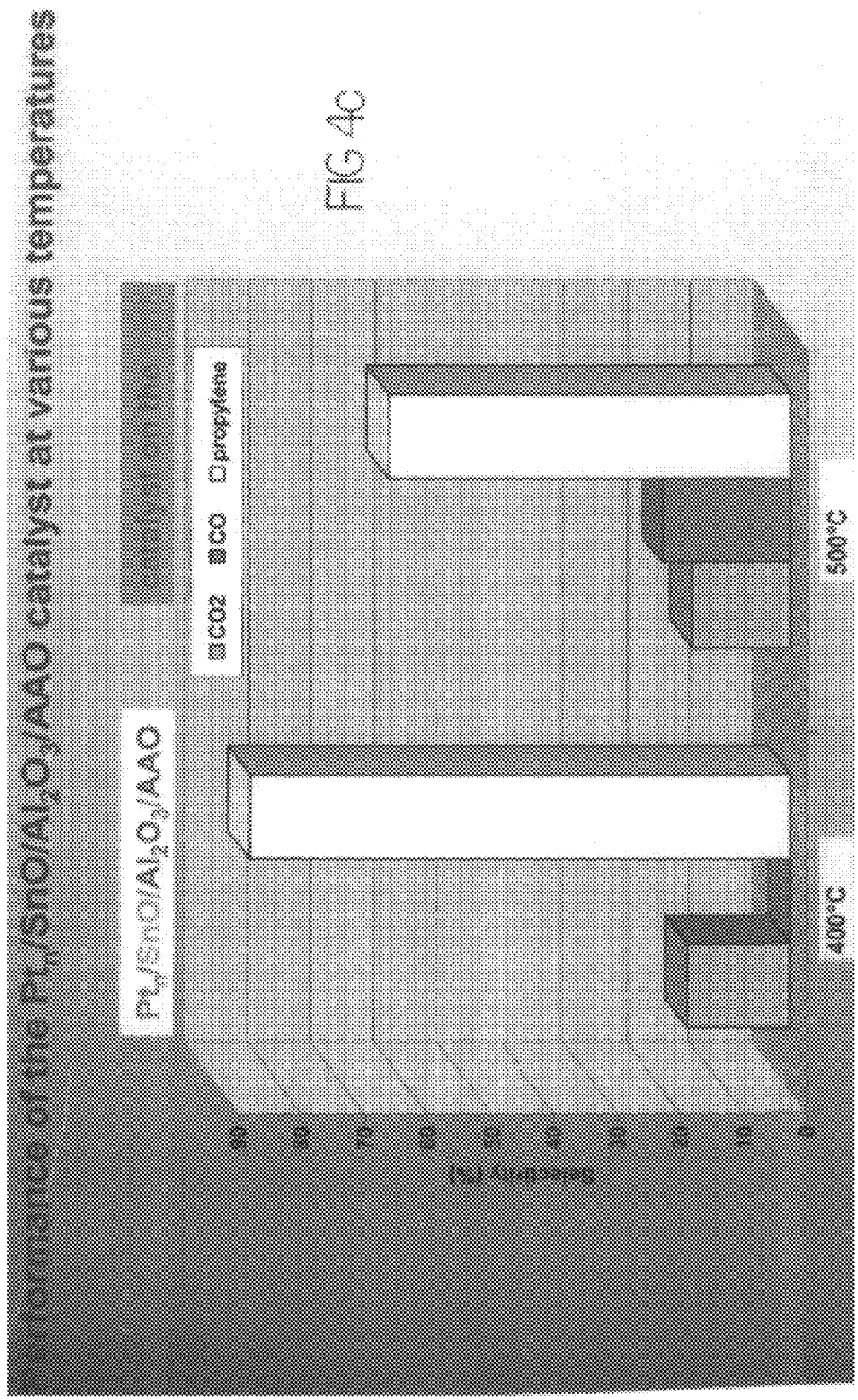

A very important advantage of cluster-beam deposition is that the location of particles on the membrane is well defined. FIG. 4B shows conversion efficiencies when catalyst clusters are positioned at the entrance of membrane pores. FIG. 4C shows conversion efficiencies when catalyst clusters are positioned at the exits of membrane pores. Generally, the clusters are arranged symmetrically about the openings, with some clusters arranged inside the pores adjacent to the openings.

Surprisingly and unexpectedly, the inventors found that having the catalytically active particle near the exit of the pore will highly increase the probability for the propane molecule undergoing only very limited number of interactions with the Pt cluster(s) prior to leaving the pore. These very short contact times of reactants with the metal clusters result in enhanced selectivity such that only parts of the reactant molecule are converted, instead of the molecule being completely cracked.

At 400° C., with Pt-clusters at the entrance of the membrane the catalyst is still highly selective, however has an approximately 8 percent lower selectivity towards propylene formation (CO emerges as the second byproduct) in comparison to the geometry with Pt-clusters at the exit of the membrane. The conversion rate was the same for the two geometries. This change can be explained by the results of studies on mass transport in the restricted space of the pores showing that in the case of a pore diameter on the order of a few tens of nm, only about 1 molecule of 10,000 entering the pore will find its way to the exit.

With catalytic particles on the entrance of the pores, the probability of increased number of collisions between the propane molecules and the catalytic particles is expected to be higher. The experimental finding underlines the importance of catalyst location for achieving significantly improved selectivity.

FIG. 3D shows the selectivity of the catalyst at 400, 500 and 550° C., with propane conversion rates up to 22% in the lower temperature conversion scenario. In the case of the $Pt_{8-10}/SnO/Al_2O_3$/AAO catalyst, the Sn:Pt ratio is by several orders of magnitude higher, which can lead to Pt-nanoparticles completely buried under the tin-oxide overlayer or spatially hinder their contact with the reactants. At 400° C., the selectivity towards propene production was 83 percent and $CO_2$ was the only byproduct. At 500° C., CO emerged as second byproduct. The selectivity observed at 400° C. clearly indicates a composition and structure of a catalyst which, if implemented, can significantly decrease the energy demand during propylene production as well as ease the separation process afterwards. The 400° C. run was made with SnO; the 500° C. run was made with SnO; and the 550° C. run was made in the absence of SnO.

At 500° C., the selectivities are very similar for both geometries (platinum clusters on the membrane entrance vs. exit) and the activity and selectivity of the catalyst did not alter after a 14 hours heat treatment under argon, thus indicating high thermal stability against sintering. The difference in selectivities observed at 400 and 500° C. can have its origin in the different reaction mechanisms involved, such as a possible onset of ignition of homogeneous pyrolysis by Pt-clusters at higher temperatures, a process accompanied by the formation of carbon monoxide.

As to oxidation of ethylene and propylene on gold and silver nanocatalysts, onset of product formation was observed between 160-200° C. At higher reaction temperatures, silver particles sintered, while gold particles stabilized with a protective alumina overcoat retained their size during the lengthy treatment.

Test results of the invention show that under-coordinated Pt sites in small $Pt_n$ clusters (i.e., clusters containing less than 10 metal atoms, or 10 atoms in total) are much more active that an extended platinum surface utilized for propane ODH. Examples of such an extended surface are large metal voils or surfaces comprising larger nanoparticles than the sizes utilized herein. This is due to the attractive interaction between the under-coordinated Pt and propane.

The inventors have calculated that the initial adsorption complex between propane and a Pt4 cluster results in significant charge transfer from a propane C—H bonding orbital to the cluster. This weakens the C—H bond as evidenced by its lengthening and a concomitant lowering of the C—H vibrational frequency by 500 cm-1. In contrast, propane is very weakly absorbed on a $Pt_{111}$ surface with essentially no C—H bond lengthening or charge transfer due to high coordination of the surface Pt atoms.

Figure 5:
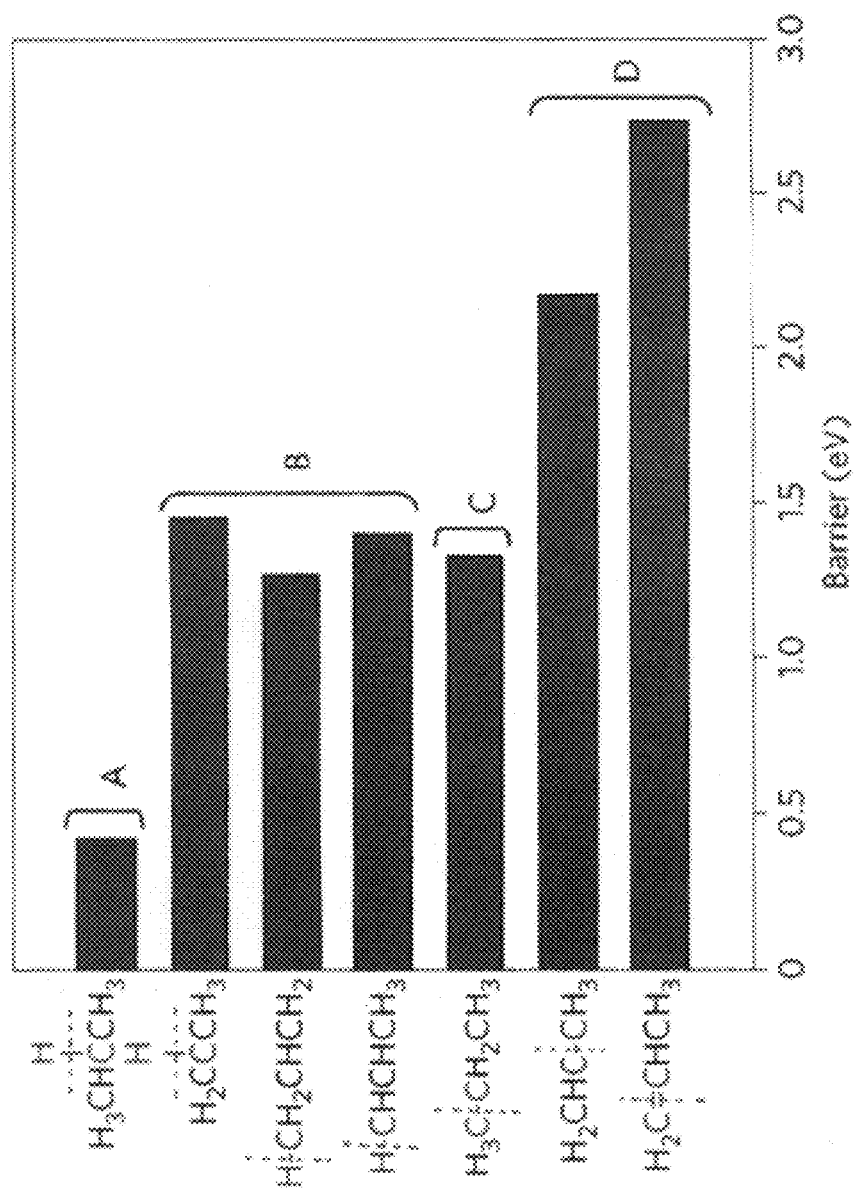
FIG. 5 is a graphical depiction of the bond breaking energy barriers associated with using the invented catalyst clusters, in accordance with features of the present invention.

FIG. 5 provides a graph of energy barriers for bond breakage at various points along the propylene molecule, in a reaction facilitated by a four-atom platinum cluster. Bonds that are broken are shown with a dashed line (- - - -). The letters A, B, C, and D correspond to the reaction channels depicted in FIG. 1. All of the barriers plotted in FIG. 5 correspond to energies relative to the reactants (propane or propylene). In propane, the C—H bond breaking on the centre carbon (A) is favoured over a terminal carbon. In propylene C—H bond breaking, all three sites (letter B) have similar barriers. Bond breaking energies are relatively low and range from 0.3 eV to 2.75 eV.

Figure 9:
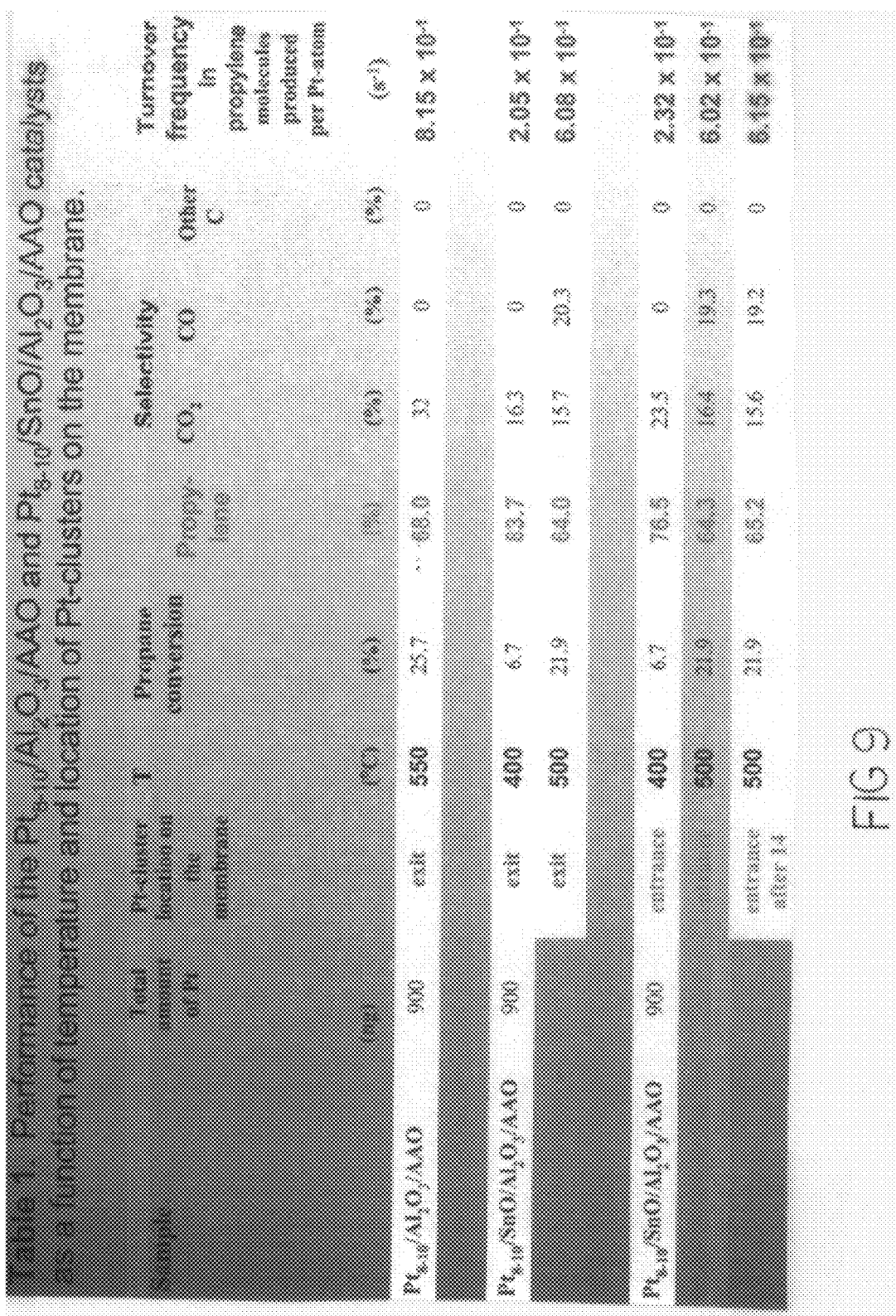
FIG. 9 is a graph of turn over frequencies of various embodiments of the catalyst constructs, in accordance with features of the present invention.

Table 1 depicted in FIG. 9, shows specific TOF values for some embodiments of the invention as a function of temperatures ranging from 400 to 550° C. TOF values depicted in Table 1 also reflect the significance of cluster placement at various locations of the pore, for example at the entrance and at the exit of the pore. The activity of the catalysts positioned at pore entrance do not vary after 14 hours exposure, as noted on the bottom of FIG. 9.

While the invention has been described with reference to details of the illustrated embodiment, these details are not intended to limit the scope of the invention as defined in the appended claims.

The invention claimed is:

1. A catalyst surface comprising:
   a) metal clusters supported on a surface of a substrate, wherein all atoms in each metal cluster are under-coordinated and contains from 4 to 12 metal atoms; and
   b) film for preventing fluid communication between the metal clusters.

2. The catalyst surface as recited in claim 1 wherein the film is integrally molded with the surface.

3. The catalyst surface as recited in claim 1 wherein the is a film positioned between the metal clusters.

4. The catalyst surface as recited in claim 3 wherein the film comprises an oxide selected from the group consisting of tin oxide, titanium oxide, zinc oxide, aluminum oxide, and combinations thereof.

5. A catalyst surface as recited in claim 1 wherein the surface comprises a construct defining pores having diameters between 1 and 20 nanometers.

6. The catalyst surface as recited in claim 5 wherein each of the pores have a first end facing a first surface of the substrate and a second end facing a second surface of the substrate and all of the metal clusters are deposited at the first ends.

7. The catalyst surface as recited in claim 5 wherein each of the pores have a first end facing a first surface of the substrate and a second end facing a second surface of the substrate and all of the metal clusters are deposited at the second ends.

8. The catalyst surface as recited in claim 5 wherein the metal clusters are positioned on the inside surfaces of the pores.

9. The catalyst surface as recited in claim 8 wherein the metal clusters project medially so as to inhibit passage of molecules larger than 180 Angstroms.

10. The catalyst surface as recited in claim 1 wherein the metal clusters consist of 8 to 10 metal atoms.

11. The catalyst surface as recited in claim 1 wherein the number of atoms forming the metal clusters are all the same.

12. The catalyst surface as recited in claim 1 wherein the metal clusters are formed on at least two surfaces to form at least two regions of reactivity, a first region of reactivity and a second region of reactivity.

13. The catalyst surface as recited in claim 12 wherein the first region of reactivity further comprises a longitudinally extending interior surface of the substrate pores, a first opening of the pores, and a second opening of the pores wherein the first opening of the pores is further comprised of a mouth rim of a pore defined by the surface of the substrate facing the direction from which reactants are flowing and the second opening of the pores is further comprised of the exit rim defined by the surface of the substrate facing the direction away from which reactants are flowing.

14. The catalyst surface as recited in claim 13 wherein the first region of reactivity provides conversions at a temperature between 400° C. and 600° C.

15. The catalyst surface as recited in claim 13 wherein the metal clusters are deposited at the first opening of the pores.

16. The catalyst surface as recited in claim 13 wherein the metal clusters are deposited at the second opening of the pores.

17. The catalyst surface as recited in claim 16 wherein metal clusters are deposited on the exterior surface.

18. The catalyst surface as recited in claim 12 wherein metal clusters are deposited on the interior surface and extend medially and toward the longitudinal axis at a distance between 0.20 nanometer and 1.0 nanometer.

19. The catalyst surface as recited in claim 18 wherein the metal clusters deposited on the interior surface have a height of at least 0.3 nanometer but less than 0.6 nanometer.

20. The catalyst surface as recited in claim 12 wherein the second region of reactivity further comprises an exterior surface of the substrate.

* * * * *